(12) United States Patent
Liu et al.

(10) Patent No.: US 7,129,708 B1
(45) Date of Patent: Oct. 31, 2006

(54) VACUUM IONIZATION GAUGE WITH HIGH SENSITIVITY

(75) Inventors: Peng Liu, Beijing (CN); Yang Wei, Beijing (CN); Lei-Mei Sheng, Beijing (CN); Liang Liu, Beijing (CN); Zhao-Fu Hu, Beijing (CN); Cai-Lin Guo, Beijing (CN); Pi-Jin Chen, Beijing (CN); Shou-Shan Fan, Beijing (CN)

(73) Assignees: Tsinghua University, Beijing (CN); HON HAI Precision Industry Co., Ltd., Tu-Cheng (TW)

( * ) Notice: Subject to any disclaimer, the term of this patent is extended or adjusted under 35 U.S.C. 154(b) by 0 days.

(21) Appl. No.: 11/187,738

(22) Filed: Jul. 22, 2005

(30) Foreign Application Priority Data

Jul. 30, 2004 (CN) .................. 2004 1 0050977

(51) Int. Cl.
*G01N 27/62* (2006.01)
(52) U.S. Cl. ..................... 324/464; 324/460
(58) Field of Classification Search ............... 324/459, 324/460, 462, 463, 464
See application file for complete search history.

(56) References Cited

U.S. PATENT DOCUMENTS 6,257,069 B1 * 7/2001 Brady et al. ................... 73/753

2005/0030044 A1 * 2/2005 Correale ..................... 324/460

OTHER PUBLICATIONS

P.A. Redhead; New Hot-Filament Ionization Gauge With Low Residual Current; pp. 173-180, vol. 3, The Journal of Vacuum Science and Technology 1996.

* cited by examiner

*Primary Examiner*—Walter Benson
(74) *Attorney, Agent, or Firm*—Tim Tingkang Xia, Esq.; Morris Manning Martin LLP

(57) ABSTRACT

A vacuum ionization gauge (30) includes a cathode (31), an anode ring (33), a shield electrode (32), an ion educed electrode (34), a reflector (35) and a collector (36). The cathode is positioned corresponding to a first opening of the shield electrode, and the ion educed electrode is positioned corresponding to an opposite second opening of the shield electrode. An ion educed hole (341) is defined in a middle of the ion educed electrode. The reflector has a curving surface generally surrounding the second opening of the shield electrode. The collector is positioned at a center of the curving surface of the reflector and points toward the ion educed hole. The anode ring is positioned in the middle of the shield electrode. The vacuum ionization gauge is small volume and has low power consumption and improved sensitivity.

20 Claims, 3 Drawing Sheets

VACUUM IONIZATION GAUGE WITH HIGH SENSITIVITY

BACKGROUND

The invention relates generally to vacuum gauges, and more particularly to a vacuum ionization gauge having improved sensitivity.

Nowadays, high vacuum conditions are employed in many technological fields of endeavor, such as in simulation technology in aerospace, superconductor technology, nuclear fusion technology, ultra-low temperature technology, and huge particle accelerator technology. Vacuum gauges for measuring pressure in ultra-high and extremely high vacuum conditions are needed.

When a standard vacuum gauge is used in ultra-high and extremely high vacuum conditions, X-ray and ions produced by means of Electron Stimulated Desorption (ESD) restrict a lowest measuring limit of the vacuum gauge to a relatively low vacuum pressure. In order to extend the lowest measuring limit of the vacuum gauge to a higher vacuum pressure, a vacuum ionization gauge is generally used. As shown in FIG. 3, a typical vacuum ionization gauge 10 includes a grid 12, a modulator 11, a filament 13, a shield 14, an ion reflector 15 and a collector 16. The top of the grid 12 is closed, and the bottom of the grid 12 is open. The modulator 11 is a short wire projecting into a center of the grid 12 from the top of the grid 12. The shield 14 is positioned at the bottom of the grid 12, and has an aperture defined in a center thereof. The ion reflector 15 is generally hemispherical, and is positioned below the shield 14. The collector 16 is a short wire projecting through a small hole in the center of the ion reflector 15.

In use, a zero voltage is applied to the grid 12 by controlling the modulator 11, a negative voltage is applied to the shield 14, and a positive voltage is applied to the ion reflector 15. The filament 13 emits electrons into the grid 12, and the electrons vibrate and collide with gas molecules. Therefore, the gas molecules are ionized to form an ion current. The ions are attracted toward the negative potential shield 14. Most of the ions pass through the aperture of the shield 14, and are focused by the positive potential on the ion reflector 15 onto the collector 16. The vacuum ionization gauge 10 utilizes the shield 14 to turn back most X-rays and ions produced by means of Electron Stimulated Desorption (ESD). Thus a lowest limit of the vacuum ionization gauge 10 can be as little as $10^{-13}$ Torr. However, the vacuum ionization gauge 10 has a complex structure, and cannot be advantageously applied in ultra-low temperature technology and huge particle accelerator technology.

Another typical vacuum ionization gauge is shown in FIG. 4. The vacuum ionization gauge 20 includes a metal shield 21, a ceramic column 27, a collector 26, an anode ring 22, and an electron emitting assembly 24. The ceramic column 27 is positioned at one end of the metal shield 21. The electron emitting assembly 24, the anode ring 22 and the collector 26 are positioned on the ceramic column 27 in turn. The electron emitting assembly 24 includes a tungsten filament 241 and a reflector 242. The vacuum ionization gauge 20 is relatively small and simple in structure, and has low power consumption. However, the vacuum ionization gauge 20 cannot turn back most X-rays and ions produced by means of Electron Stimulated Desorption (ESD). This restricts a lowest measuring limit of the vacuum ionization gauge 20 to a relatively low vacuum pressure.

What is needed, therefore, is a vacuum ionization gauge which solves the above-described disadvantages and has improved sensitivity.

SUMMARY

In an embodiment, a vacuum ionization gauge includes a cathode, an anode ring, a shield electrode, an ion educed electrode, a reflector and a collector. The cathode is positioned corresponding to a first opening of the shield electrode, and the ion educed electrode is positioned corresponding to an opposite second opening of the shield electrode. An ion educed hole is defined in a middle of the ion educed electrode. The reflector has a curving surface generally surrounding the second opening of the shield electrode. The collector is positioned at a center of the curving surface of the reflector and points toward the ion educed hole. The anode ring is positioned in the middle of the shield electrode.

Compared with a conventional vacuum ionization gauge, the vacuum ionization gauges of the embodiments of the present invention have the following advantages. Firstly, the shield electrode and the ion educed electrode cooperatively define a semi-closed cylinder, within which electrons can be readily vibrated. This contributes to improved sensitivity of the vacuum ionization gauge. Secondly, the reflector enables more ions produced by means of Temperature Programmed Desorption (TPD) to reach the collector, which also contributes to improved sensitivity of the vacuum ionization gauge. Thirdly, the ion educed electrode can turn back most X-rays and ions produced by means of Electron Stimulated Desorption (ESD). This ensures that a lowest measuring limit of the vacuum ionization gauge can be extended to a higher vacuum pressure. Furthermore, when the cathode is a cold cathode, the vacuum ionization gauge has low power consumption.

Other advantages and novel features will become more apparent from the following detailed description when taken in conjunction with the accompanying drawings, in which:

DETAILED DESCRIPTION OF EMBODIMENTS

Reference will now be made to the drawings to describe embodiments of the present invention in detail.

Figure 1:
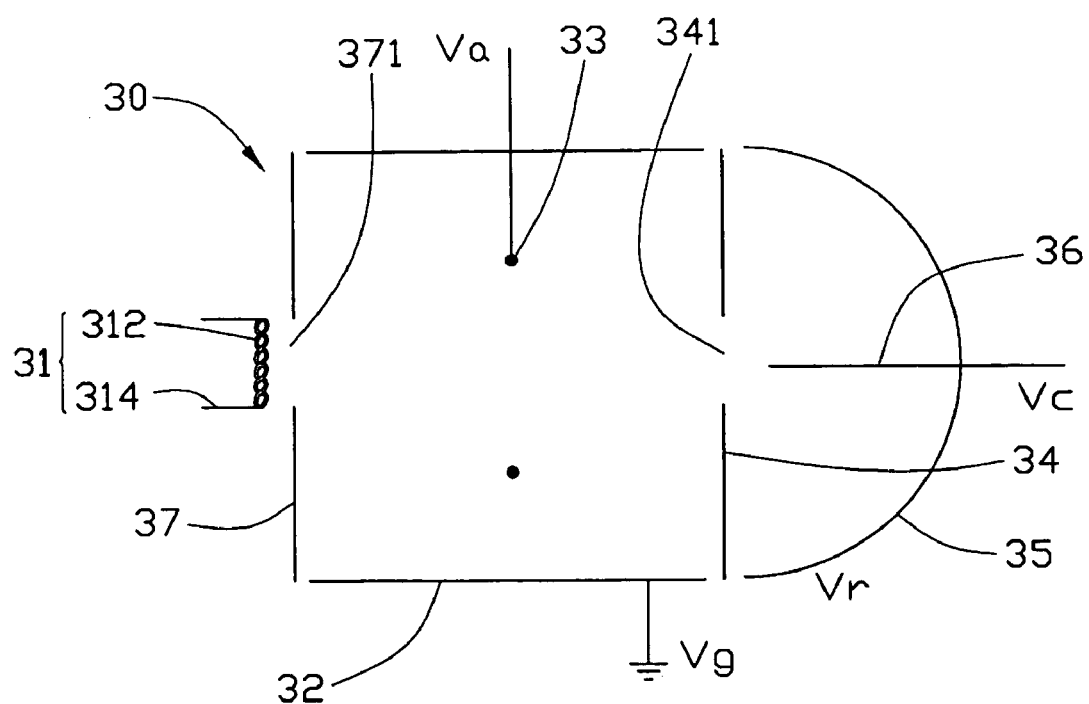
FIG. 1 is a schematic, side cross-sectional view of a vacuum ionization gauge in accordance with a first embodiment of the present invention.

Referring to FIG. 1, a vacuum ionization gauge 30 for measuring a vacuum condition of an object in accordance with a first embodiment of the present invention includes a hot cathode 31, an anode ring 33, a shield electrode 32, an ion educed electrode 34, a reflector 35 and a collector 36. The shield electrode 32 is generally cylindrical, and includes a first opening (not labeled) and an opposite second opening (not labeled). The hot cathode 31 is positioned corresponding to the first opening of the shield electrode 32, and the ion educed electrode 34 is positioned corresponding to the second opening of the shield electrode 32. An ion educed hole 341 is defined in a middle of the ion educed electrode 34. The reflector 35 has a curving surface (not labeled) generally surrounding the second opening of the shield electrode 32. The collector 36 is positioned at a center of the curving surface of the reflector 35, and points toward the ion educed hole 341. The anode ring 33 is positioned in the shield electrode 32.

The hot cathode 31 includes a tungsten filament 312, and a pair of supporting poles 314 for supporting the tungsten filament 312. The tungsten filament 312 has an externally-sourced voltage applied thereto. When the tungsten filament 312 is heated, electrons are emitted therefrom into the shield electrode 32. A diameter of the shield electrode 32 is about 18 millimeters, and a length thereof is about 18 millimeters. The anode ring 33 has an externally-sourced voltage applied thereto. A diameter of the anode ring 33 is about 9 millimeters. In general, the anode ring 33 is a wire. In the first embodiment, a diameter of the wire is about 200 micrometers. In order to form a symmetrical electric field, the anode ring 33 is preferably positioned in a middle of the shield electrode 32, and is kept electrically insulated from the shield electrode 32.

The ion educed electrode 34 is annular. The ion educed electrode 34 generally covers the second opening of the shield electrode 32, and is kept electrically insulated from the shield electrode 32. A size of the ion educed hole 341 is configured to ensure that: (i) more ions produced by means of Temperature Programmed Desorption (TPD) reach the collector 36; and (ii) most X-rays and ions produced by means of Electron Stimulated Desorption (ESD) are turned back. In the first embodiment, the reflector 35 is hemispherical, and a diameter thereof is about 18 millimeters. The reflector 35 surrounds the second opening of the shield electrode 32, and is kept electrically insulated from the ion educed electrode 34. A small opening (not labeled) is defined in the center of the reflector 35, for holding the collector 36 therein. The collector 36 is generally a wire, and is kept electrically insulated from the reflector 35. In the first embodiment, a diameter of the wire is about 200 micrometers. A tip of the collector 36 is aimed at the ion educed hole 341.

The anode ring 33, ion educed electrode 34 and reflector 35 are all axially aligned along an axis of the shield electrode 32. The vacuum ionization gauge 30 can further include an electron induct electrode 37. The electron induct electrode 37 is annular. The electron induct electrode 37 generally covers the first opening of the shield electrode 32, and is kept electrically insulated from the shield electrode 32. An electron induct hole 371 is defined in a middle of the electron induct electrode 37. A diameter of the electron induct hole 371 is same as that of the ion educed hole 341.

In use, different voltages are applied to the shield electrode 32, anode ring 33, collector 36 and reflector 35. For example, the shield electrode 32 is grounded, about 1 kilovolt is applied to the anode ring 33 to form a symmetrical electric field in the shield electrode 32, the voltage of the collector 36 is zero, and the voltage of the reflector 35 is positive. Furthermore, the voltage of the hot cathode 31 is positive, and the voltages of the electron induct electrode 37 and the ion educed electrode 34 are determined according to actual need.

An operating process of the vacuum ionization gauge 30 is as follows. Firstly, the hot cathode 31 emits electrons into the shield electrode 32 via the electron induct hole 371. Secondly, the electrons vibrate in the symmetrical electric field, and collide with gas molecules and ionize the gas molecules to form an ion current. These ions are produced by means of Temperature Programmed Desorption (TPD). Thirdly, the ion current moves out of the shield electrode 32 via the ion educed hole 341, and the ions are collected by the collector 36 to form a current signal of the collector 36. The current is directly proportional to a vacuum pressure in the vacuum ionization gauge 30. Therefore, the vacuum pressure in the vacuum ionization gauge 30 can be measured according to this relation.

Figure 2:
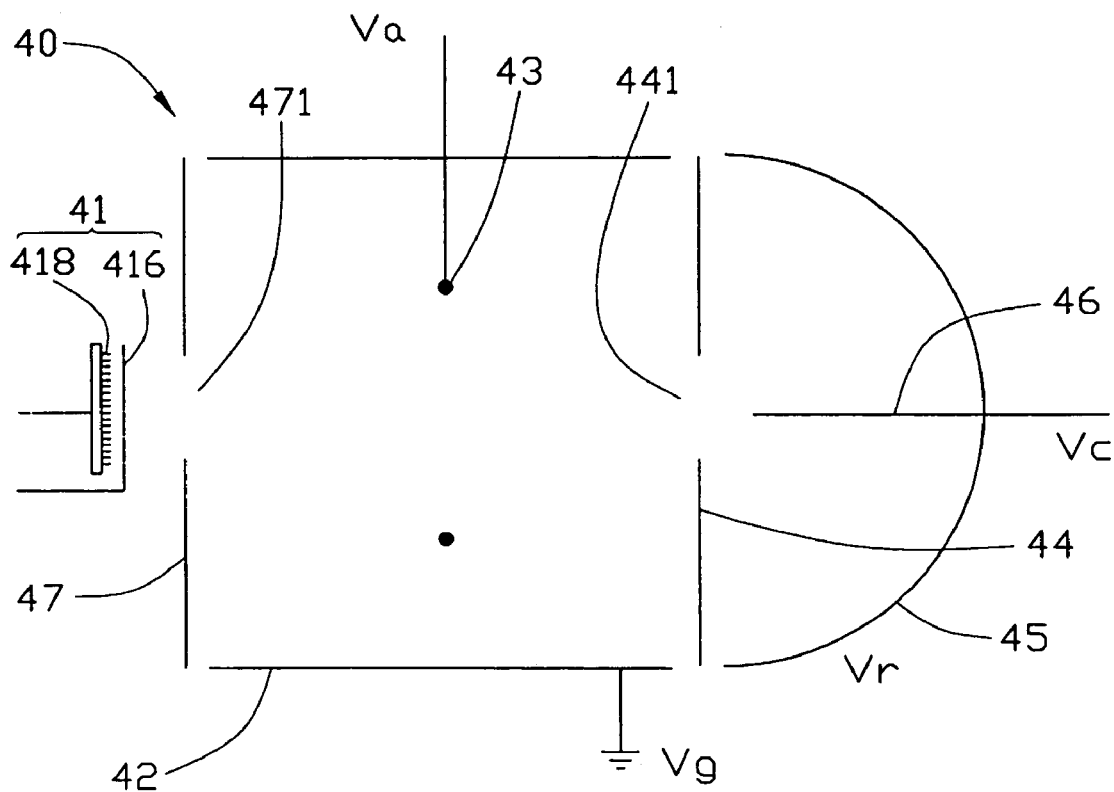
FIG. 2 is a schematic, side cross-sectional view of a vacuum ionization gauge in accordance with a second embodiment of the present invention.
Figure 3:
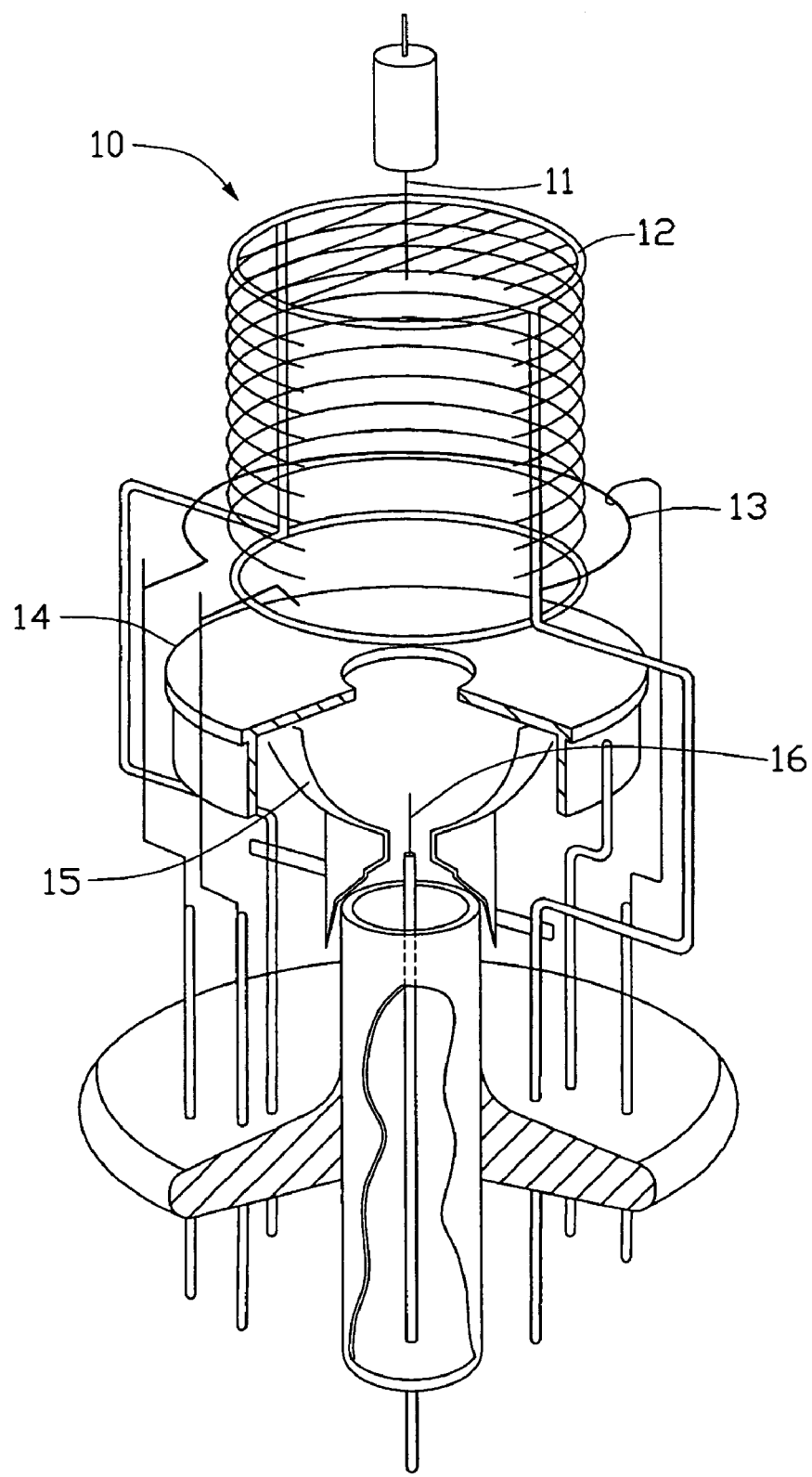
FIG. 3 is a schematic, isometric cut-away view of a conventional vacuum ionization gauge.
Figure 4:
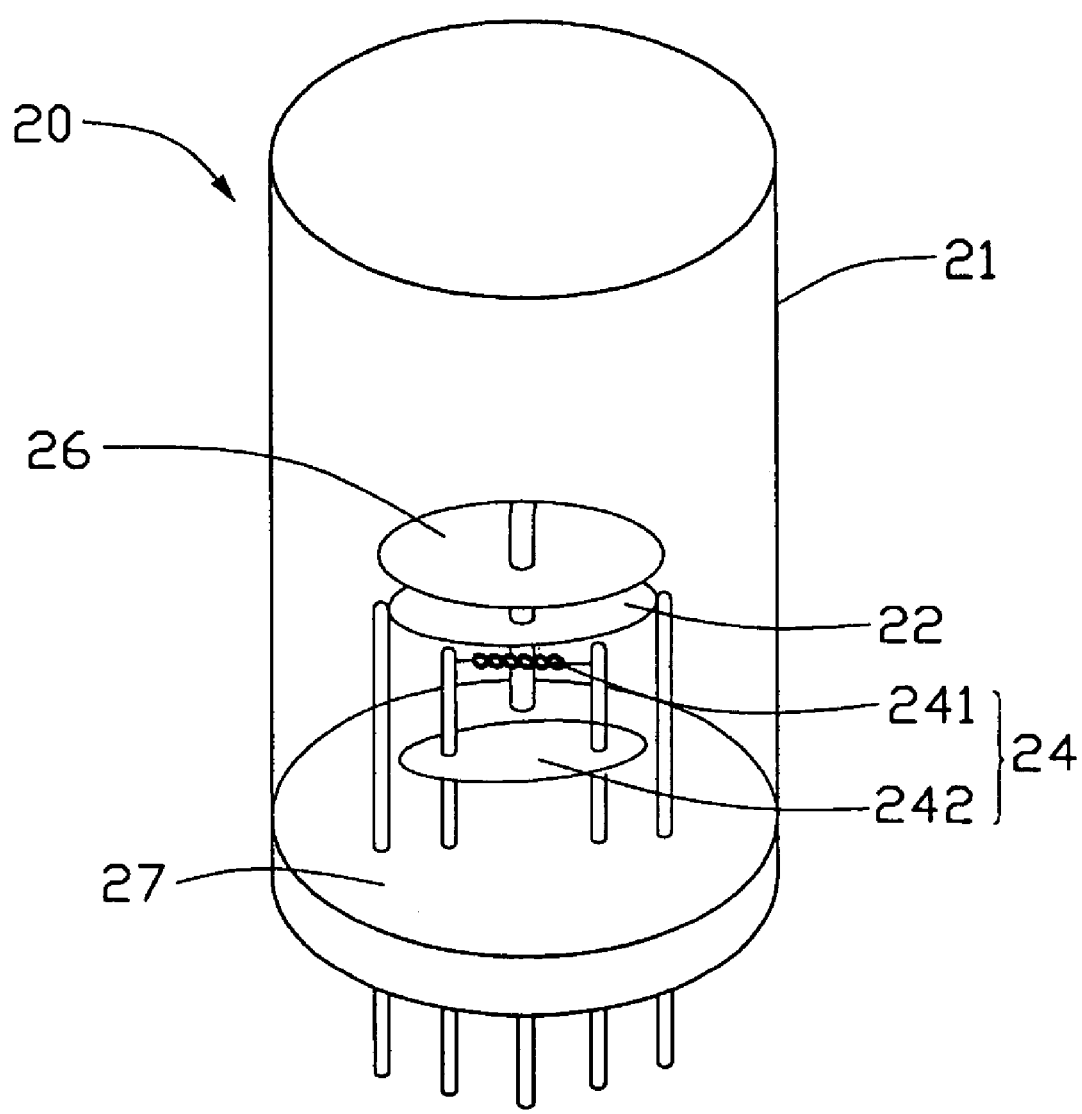
FIG. 4 is a schematic, isometric view of another conventional vacuum ionization gauge, showing components contained within a metal shield thereof.

Referring to FIG. 2, a vacuum ionization gauge 40 in accordance with a second embodiment of the present invention includes a cold cathode 41, an anode ring 43, a shield electrode 42, an ion educed electrode 44, a reflector 45 and a collector 46. The shield electrode 42 is generally cylindrical, and includes a first opening (not labeled) and an opposite second opening (not labeled). The cold cathode 41 is positioned corresponding to the first opening of the shield electrode 42, and the ion educed electrode 44 is positioned corresponding to the second opening of the shield electrode 42. An ion educed hole 441 is defined in a middle of the ion educed electrode 44. The reflector 45 has a curving surface (not labeled) generally surrounding the second opening of the shield electrode 42. The collector 46 is positioned at a center of the curving surface of the reflector 45, and points toward the ion educed hole 441. The anode ring 43 is positioned in the shield electrode 42. The vacuum ionization gauge 40 can further include an electron induct electrode 47. The electron induct electrode 47 is annular. The electron induct electrode 47 generally covers the first opening of the shield electrode 42, and is kept electrically insulated from the shield electrode 42. An electron induct hole 471 is defined in a middle of the electron induct electrode 47. A diameter of the electron induct hole 471 is the same as that of the ion educed hole 441.

As will be appreciated, a structure of the vacuum ionization gauge 40 is similar to that of the vacuum ionization gauge 30, except that the hot cathode 31 of the vacuum ionization gauge 30 is replaced by the cold cathode 41 of the vacuum ionization gauge 40. The cold cathode 41 includes a substrate (not labeled), a field emission array 418 formed on the substrate, and a grid electrode 416 corresponding to the field emission array 418. The field emission array 418 is aimed at the electron induct hole 471. The field emission array 418 has a needle structure or a film structure, which may for example be metallic needles, nonmetallic needles, compound needles, nanotubes, nanorods, or diamond films. The grid electrode 416 has an aperture structure, which may for example comprise metallic rings, metallic-enclosed apertures, or a metallic net. In general, the cold cathode 41 only includes the substrate and the field emission array 418 formed on the substrate. With this configuration, the electron induct hole 471 accordingly has a net structure.

An operating process of the vacuum ionization gauge 40 is as follows. Firstly, the cold cathode 41 emits electrons into the shield electrode 42 via the electron induct hole 471. Secondly, the electrons vibrate in the symmetrical electric field, and collide with gas molecules and ionize the gas molecules to form an ion current. These ions are produced by means of Temperature Programmed Desorption (TPD). Thirdly, the ion current moves out of the shield electrode 42 via the ion educed hole 441, and the ions are collected by the collector 46 to form a current signal of the collector 46. The current is directly proportional to a vacuum pressure in the vacuum ionization gauge 40. Therefore, the vacuum pressure in the vacuum ionization gauge 40 can be measured according to this relation.

Compared with a conventional vacuum ionization gauge, the vacuum ionization gauges 30, 40 of the embodiments of the present invention have the following advantages. Firstly, the shield electrode 32, 42 and the ion educed electrode 34, 44 cooperatively define a semi-closed cylinder, within which electrons can be readily vibrated. This contributes to improved sensitivity of the vacuum ionization gauge 30, 40. Secondly, the reflector 35, 45 enables more ions produced by means of Temperature Programmed Desorption (TPD) to reach the collector 36, 46, which also contributes to improved sensitivity of the vacuum ionization gauge 30, 40. Thirdly, the ion educed electrode 34, 44 can turn back most X-rays and ions produced by means of Electron Stimulated Desorption (ESD). This ensures that a lowest measuring limit of the vacuum ionization gauge 30, 40 can be extended to a higher vacuum pressure. Furthermore, because the vacuum ionization gauge 40 uses the cold cathode 41, the vacuum ionization gauge 40 has low power consumption.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

We claim:

1. A vacuum ionization gauge comprising:
   a shield electrode having a first opening and a second opening;
   a cathode unit positioned corresponding to the first opening of the shield electrode;
   an ion educed electrode positioned corresponding to the second opening of the shield electrode;
   an ion educed hole defined in a middle of the ion educed electrode;
   a reflector generally surrounding the second opening of the shield electrode;
   a collector positioned at a middle of the reflector and pointing toward the ion educed hole; and
   an anode positioned in the shield electrode.

2. The vacuum ionization gauge as claimed in claim 1, further comprising an electron induct electrode associated with the first opening of the shield electrode.

3. The vacuum ionization gauge as claimed in claim 2, wherein a middle of the electron induct electrode defines an electron induct hole, and a diameter of the electron induct hole is substantially the same as a diameter of the ion educed hole.

4. The vacuum ionization gauge as claimed in claim 1, wherein the cathode unit is a hot cathode.

5. The vacuum ionization gauge as claimed in claim 4, wherein the hot cathode comprises a tungsten filament, and a plurality of supporting poles for supporting the tungsten filament.

6. The vacuum ionization gauge as claimed in claim 1, wherein the cathode unit is a cold cathode.

7. The vacuum ionization gauge as claimed in claim 6, wherein the cold cathode comprises a substrate, and a field emission array formed on the substrate.

8. The vacuum ionization gauge as claimed in claim 7, wherein the field emission array comprises any one or more of metallic needles, nonmetallic needles, compound needles, nanotubes, nanorods, and/or diamond films.

9. The vacuum ionization gauge as claimed in claim 7, wherein the cold cathode further comprises a grid electrode corresponding to the field emission array.

10. The vacuum ionization gauge as claimed in claim 9, wherein the grid electrode comprises metallic rings, metallic-enclosed apertures, or a metallic net.

11. The vacuum ionization gauge as claimed in claim 1, wherein the shield electrode is generally cylindrical, and is grounded.

12. The vacuum ionization gauge as claimed in claim 11, wherein a diameter of the shield electrode is about 18 millimeters, and a length of the shield electrode is about 18 millimeters.

13. The vacuum ionization gauge as claimed in claim 1, wherein the reflector is hemispherical, and is adapted for having a positive voltage applied thereto.

14. The vacuum ionization gauge as claimed in claim 1, wherein the collector comprises a wire, and a zero voltage is applied thereto.

15. The vacuum ionization gauge as claimed in claim 1, wherein the anode is an anode ring.

16. The vacuum ionization gauge as claimed in claim 15, wherein the anode ring comprises a wire, and is adapted for having a high voltage of about 1 kilovolt applied thereto.

17. The vacuum ionization gauge as claimed in claim 1, wherein the anode, ion educed electrode and reflector are all axially aligned along an axis of the shield electrode.

18. A gauge for measuring a vacuum condition of an object, comprising:
   a shield electrode defining a space therein to be communicable with an object to be measured;
   a cathode unit disposed next to said space and electrifiable to emit electrons into said space of said shield electrode;
   an anode disposed in said space and spaced from said shield electrode and said cathode unit, and electrifiable to urge said electrons from said cathode unit to interact with available gas molecules from said object in said space for generating ionized gas molecules;
   an ion educed electrode comprising an ion educed hole defined therein, said ion educed electrode disposed beside said anode and spaced opposite to said cathode unit to allow ionized gas molecules to pass through said ion educed hole
   a collector separated from said space by said ion educed electrode and capable of collecting said ionized gas molecules passing through said ion educed hole of said ion educed electrode so as to determine a vacuum condition of said object; and
   a reflector surrounding said ion educed electrode and said collector to facilitate said ionized gas molecules to reach said collector.

19. The gauge as claimed in claim 18, wherein said cathode unit is selected from a hot cathode unit and a cold cathode unit.

20. The gauge as claimed in claim 18, further comprising an electron induct electrode with an electron induct hole defined therein, said electron induct electrode disposed between said cathode unit and said anode.

* * * * *